US006756344B2

(12) United States Patent
Killick et al.

(10) Patent No.: US 6,756,344 B2
(45) Date of Patent: Jun. 29, 2004

(54) PLANT GROWTH HORMONE COMPOSITIONS

(75) Inventors: Robert William Killick, Mount Waverley (AU); Andrew Robert Killick, Richmond (AU); Peter William Jones, Menzies Creek (AU); Peter Ronald Wrigley, Blackburn (AU); John David Morrison, Thomastown (AU)

(73) Assignee: Victorian Chemicals International Pty Ltd, Richmond (AU)

( * ) Notice: Subject to any disclaimer, the term of this patent is extended or adjusted under 35 U.S.C. 154(b) by 0 days.

(21) Appl. No.: 10/204,620

(22) PCT Filed: Feb. 13, 2001

(86) PCT No.: PCT/AU01/00130

§ 371 (c)(1),
(2), (4) Date: Aug. 21, 2002

(87) PCT Pub. No.: WO01/62080

PCT Pub. Date: Aug. 30, 2001

(65) Prior Publication Data

US 2003/0013610 A1 Jan. 16, 2003

(30) Foreign Application Priority Data

Feb. 23, 2000 (AU) .............................................. PQ5798

(51) Int. Cl.⁷ ........................ A01N 45/02; A01N 43/90; A01N 25/30
(52) U.S. Cl. ........................ 504/297; 504/320; 504/348; 504/353
(58) Field of Search ............................... 504/297, 320, 504/348, 353

(56) References Cited

U.S. PATENT DOCUMENTS

| | | | |
|---|---|---|---|
| 4,154,596 A | 5/1979 | George et al. .................. | 71/89 |
| 4,853,026 A | 8/1989 | Frisch et al. .................... | 71/86 |
| 4,984,874 A | 1/1991 | Yamamoto et al. ......... | 350/334 |
| 5,411,932 A | 5/1995 | Yoshida et al. ............. | 504/132 |
| 5,672,564 A | 9/1997 | Wigger et al. ............. | 504/116 |
| 6,068,849 A * | 5/2000 | Mueninghoff et al. ...... | 424/405 |
| 6,133,199 A | 10/2000 | Soula et al. ................. | 504/206 |
| 6,239,073 B1 * | 5/2001 | Back et al. .................. | 504/138 |
| 2001/0019996 A1 | 9/2001 | Soula et al. ................. | 504/189 |

FOREIGN PATENT DOCUMENTS

| | | |
|---|---|---|
| AU | 674464 | 12/1996 |
| EP | 508 022 | 10/1992 |
| EP | 554 015 | 8/1993 |
| EP | 358 494 | 3/1994 |
| EP | 598 404 | 5/1994 |
| EP | 598 515 | 5/1994 |
| EP | 0933025 A | 8/1999 |
| EP | 933 025 | 8/1999 |
| WO | WO 90/07272 | 7/1990 |
| WO | WO 93/00809 | 1/1993 |
| WO | WO 96/01049 A | 1/1996 |
| WO | WO 96/01049 | 1/1996 |
| WO | WO 97/00010 | 1/1997 |
| WO | WO 98/09518 | 3/1998 |
| WO | WO 98/17110 | 4/1998 |
| WO | WO 98/53680 | 12/1998 |
| WO | WO 99/00012 | 1/1999 |
| WO | WO 99/05914 | 2/1999 |
| WO | WO 99/51099 | 10/1999 |
| WO | WO 00/05953 A | 2/2000 |
| WO | WO 00/05953 | 2/2000 |
| WO | WO 00/32045 | 6/2000 |
| WO | WO 00/67571 | 11/2000 |
| WO | WO 00 67571 A | 11/2000 |

OTHER PUBLICATIONS

Roger S. Young, "Improve 'Promalin' Response with Adjuvants", Proc Plant Growth Regul Work Group, (1978), vol. 5, pp. 221–224.

Charles W. Coggins, et al., "Possible Methods to Increase Efficacy of Gibberellic Acid Applied to Navel Orange Trees", Adjuvants for Agrichemicals, Chapter 55, 1992, pp. 567–572.

P. M. Tabbush, et al., "Chemicals for the Forester: What about Additives", Forestry and British Timber, Feb. 1986, pp. 12–13.

D.J. Turner, "Additives for Use with Herbicides, a Review", AFRC Weed Research Organisation, J. P. Prat. Troples 1984, 1(2): 77–86,.

D.J. Turner, et al., "Studies with Solubilised Herbicide Formulations", Proceedings 12th British Weed Control Conference, (1974), pp. 177–185.

D.J. Turner, et al., "Studies with Alternative Glyphosate Formulations", 1985 BCPC Monogram No. 28, Symposioum on Application and Biology, pp. 2–13.

D.J. Turner, "Preliminary Results of Research into Improving Herbicide Performance by the Use of Additives", Weed Research Organization, Oxford, UK, 1976, pp. 89–91.

Derwent–ACC–No: 1983–49777K (Feb. 12, 1983), Abstracting JP 58023898 A, dated Feb. 12, 1983.

* cited by examiner

Primary Examiner—S. Mark Clardy
(74) Attorney, Agent, or Firm—Drinker Biddle & Reath LLP

(57) ABSTRACT

A plant growth promoter composition is provided comprising: (a) not in excess of 20% by weight of one or more gibberellins; and (b) an essentially non-aqueous solvent system comprising: (i) 30 to 99% by weight of one or more lipophilic solvents; (ii) at least an equivalent molar amount to the gibberellins of one or more lipophilic alkaline coupling agents which enable the gibberellins to form a lipophilic solvent soluble complex; (iii) 1 to 50% by weight of one or more emulsifiers which blend with the lipophilic solvent(s) to form a homogeneous product and enable dispersion of the composition into water for application; and (iv) optionally, not in excess of 15% by weight of one or more viscosity reducing co-solvents.

26 Claims, No Drawings

PLANT GROWTH HORMONE COMPOSITIONS

FIELD OF THE INVENTION

This invention relates to plant growth hormone compositions. More particularly, the present invention relates to gibberellin compositions and a method of increasing the efficacy of gibberellins.

BACKGROUND OF THE INVENTION

In this specification, where a document, act or item of knowledge is referred to or discussed, this reference or discussion is not an admission that the document, act or item of knowledge or any combination thereof was at the priority date:

(i) part of common general knowledge; or
(ii) known to be relevant to an attempt to solve any problem with which this specification is concerned.

The agricultural industry has found that the use of plant growth hormones can aid in the control of crop quality and thus the value of the harvest. Plant growth hormones evidence several effects including the ability to either stimulate or inhibit growth. There are five major groups of plant hormones: auxins, gibberellins, ethylene, cytokinins and abscisic acid. The more commonly used groups in agriculture at the moment are the auxins, gibberellins, ethylene and cytokinins.

The gibberellins, which include gibberellic acid or GA-3, are responsible for promoting growth in most plants. They are, for example, known to cause growth in dwarf mutants so that they are indistinguishable from normal tall, non-mutant plants. Seed germination can be hastened by application of gibberellins. Some plants have different juvenile and adult growth and gibberellins applied to a bud on adult growth will cause formation of juvenile growth. Application to plants which form rosettes before flowering will induce bolting and flowering. Gibberellins also stimulate pollen germination. Parthenocarpic fruit can be caused by gibberellins in some fruits such as apples, currants, cucumbers, eggplants, mandarin oranges, almonds and peaches.

Gibberellins are used commercially to increase fruit size and their set and cluster sizes. For example, application of gibberellins to grapes is well known. It also induces a much looser appearance to the cluster of grapes. Other areas of known uses of gibberellins include delaying the ripening of citrus fruit on trees, stimulating flowering of strawberries and stimulating the partial digestion of starches in germinating barley during the process of brewing beer.

The gibberellins cannot be easily directly applied to a crop and require a solvent system as a carrier for such applications. Further, gibberellins are slowly hydrolysed in aqueous solutions and therefore cannot be stored long term in aqueous solutions. Commercial solutions are thus non-aqueous. Gibberellins are currently dissolved in alcohol solutions, particularly methanol. Methanol is both flammable and poisonous. The Dangerous Goods Authorities therefore demand that all products which contain methanol, including gibberellin solutions, be marked as both flammable and poisonous and handled accordingly.

For application, the farmer dilutes the methanol gibberellin (usually gibberellic acid) solution with water and then this is sprayed onto the crop. Numerous applications of this gibberellin spray are necessary to achieve the desired effects. When used on grape vines, the first applications, typically two, are termed thinning sprays because their timing is designed to reduce the number of grapes per bunch. The later applications are used to increase the size of the grapes and are called sizing sprays. It is recognised that whilst the gibberellin is 'taken-up' through the foliage of the plant, the cuticle of the foliage is covered with a thin layer of wax which renders it hydrophobic and difficult to permeate. As a result, the uptake by the foliage of gibberellin in an aqueous solution is not efficient. This inefficiency is further increased when the methanol and water have evaporated leaving the gibberellin as a 'deposit' on the foliage. As gibberellins are expensive, the farmer is always balancing the cost of such applications against the increase in the price of the fruit that may be achieved.

In relation to fruits (eg. grapes, citrus fruits and strawberries), their perceived quality and thus sale value is measured in part by the size and colour of the fruit. A cost-effective method which would
  increase the size of fruit;
  achieve fruit maturity at an earlier date; and
  eliminate any undesirable flammable/poisonous carrier would therefore be of value to the grape grower.

Accordingly, investigations have been carried out in an effort to achieve one or more of these goals.

SUMMARY OF THE INVENTION

It has been found that the lack of solubility of gibberellins in lipophilic solvents has been overcome through the use of certain lipophilic solvent systems. This is of interest because they are not flammable like the lower alcohols such as methanol.

According to the invention, a plant growth promoter composition is provided comprising:
(a) not in excess of 20% by weight of one or more gibberellins; and
(b) an essentially non-aqueous solvent system comprising:
  (i) 30 to 99% by weight of one or more lipophilic solvents;
  (ii) at least an equivalent molar amount to the gibberellin(s) of one or more lipophilic alkaline coupling agents which enable the gibberellin(s) to form a lipophilic solvent soluble complex;
  (iii) 1 to 50% by weight of one or more emulsifiers which blend with the lipophilic solvent(s) to form a homogeneous product and enable dispersion of the composition into water for application; and
  (iv) optionally, not in excess of 15% by weight of one or more viscosity reducing co-solvents.

It was further found that when gibberellins are used with this solvent system, the growth promoting activity of gibberellins in fruit, and in particular grapes, is enhanced. In particular, use of the solvent system produces grape berries of earlier maturity, larger dimensions and a better appearance showing less russetting (pitting) and less discoloration.

According to a second aspect of the invention there is provided a method for enhancing the efficacy of at least one gibberellin acting as a plant growth promoter comprising the step of incorporating gibberellins into plant growth promoter compositions comprising:
(a) an essentially non-aqueous solvent system comprising:
  (i) 30 to 99% by weight of the total composition of one or more lipophilic solvents;
  (ii) at least an equivalent molar amount to the gibberellin(s) of one or more lipophilic alkaline coupling agents which enable the gibberellin(s) to form a lipophilic solvent soluble complex;

(iii) 1 to 50% by weight of the total composition of one or more emulsifiers which blend with the lipophilic solvent(s) to form a homogeneous product and enable dispersion of the composition into water for application; and (iv) optionally, not in excess of 15% by weight of the total composition of one or more viscosity reducing co-solvents.

The gibberellins may be any member of the gibberellin family known to those skilled in the art. Preferably, the gibberellin is gibberellic acid (Gibberellin A-3). Preferably, the amount of gibberellins is in the range of 1 to 15% by weight. More preferably, the amount of gibberellins is in the range of 4 to 10% by weight. The current commercial products contain either 4 or 10% by weight gibberellins.

The lipophilic solvents which can be used include mineral oils, waxes and other petroleum fractions; vegetable and animal oils, fats and waxes and their simple esters; and fatty alcohols and/or synthetic branched chain alcohols and their esters. Preferably, the amount of lipophilic solvent is in the range of 40 to 80% by weight of the total composition.

Preferably, the lipophilic solvents are esters of vegetable oils, in particular, one or more alkyl esters of fatty acids, such as ethyl oleate. There are innumerable variations of the esters of vegetable oils since the alkyl esters of fatty acids may be produced from the combination of any one or more of the lower alcohols whilst the fatty acid moiety can be derived from the natural oils and fats such as lard, tallow and vegetable oils or from specific blends produced by fatty acid manufacturers or from fatty acids produced by synthetic means or their blends. Readily available commercial vegetable oils such as canola, corn, sunflower and soyabean oils are also sources for fatty acids.

Typically, the lipophilic alkaline coupling agents are selected from the following lipophilic solvent soluble bases:

(a) quaternary ammonium hydroxides, overbased phenates, overbased sulphonates;

(b) aromatic, arylalkyl, alkylaryl and polycyclic amines; and (c) fatty amines and fatty imidazolines.

A suitable commercially available lipophilic alkaline coupling agent is dimethyl cocoamine. Preferably, the lipophilic alkaline coupling agent is a mixture of dimethyl cocoamine and oleylamine. Preferably, the amount of lipophilic alkaline coupling agent used is a molar excess to the amount of gibberellins used. Typically, the amount of lipophilic alkaline coupling agent is in 30% molar excess to the amount of gibberellins.

The properties of the emulsifier system which comprises one or more emulsifiers, will be well known to those skilled in the art and it is recognised that there are a multitude of suitable combinations. Those skilled in the art will note that emulsifiers of certain types may disturb the lipophilic solvent soluble complex, eg acids or anionics, and that these emulsifiers should be avoided. The emulsifier system will be easily blended with the lipophilic solvents to furnish a homogeneous product and to enable dispersion, into water for application. Families of emulsifiers known to provide suitable emulsification of such lipophilic solvents include sorbitan esters and ethoxylates, alcohol ethoxylates, fatty acid ethoxylates (PEG esters), difatty alkyl imidazoline derivatives and fatty betaines. It is recognised that other surfactant types either alone or in combinations may also provide suitable emulsification. Preferably, the amount of emulsifiers used is in the range from 3 to 20% by weight of the total composition.

Viscosity reducing co-solvents will be known to those skilled in the art and include simple alcohols and monoalkyl ethers. If a high flash point is to be maintained, the viscosity reducing co-solvent should be a glycol, diglycol or diglycol ether.

EXAMPLES

The invention will now be further illustrated with reference to the following non-limiting examples.

The examples use the following components.

| | |
|---|---|
| AT 1214 | Dimethyl cocoamine ex Procter & Gamble, U.S.A. |
| Butyl Diglysolv | Diethylene glycol mono butyl ether ex Huntsman, Australia |
| Butyl Glysolv | Ethylene glycol mono butyl ether ex Huntsman, Australia. |
| Ecoteric T-80 | Sorbitan monooleate 20 moles EO ex Huntsman, Australia |
| Esterol 123 | 80% ethyl oleate and 20% methyl oleate ex Victorian Chemicals, Australia |
| Esterol 244 | PEG 400 dioleate ex Victorian Chemicals, Australia |
| Ethanol | Anhydrous industrial methylated spirits SGF3 ex CSR, Australia |
| Ethyl Diglysolv | Diethylene glycol mono ethyl ether ex Huntsman, Australia. |
| GA 4/7 | mixture of two gibberellins of 96% purity ex Agtrol USA |
| Gibberellic acid | 90% technical grade Gibberellin A-3 powder ex Krishi Rasayan, India or Agtrol, SUA |
| Glysolv DPM | Dipropylene glycol mono methyl ether ex Huntsman, Australia |
| ProGibb 4 | 4% Gibberellin A-3 in methanol ex Abbott Labs, U.S.A. |
| ProGibb 10 | 10% Gibberellin A-3 in methanol ex Abbott Labs, U.S.A. |
| NORAM-O | Oleylamine; 9-octadecen-l-amine, (Z) ex Elf Atochem, France |
| X-77 | Alcohol ethoxylate ex Aventis, Australia |

Example 1

In this example, a homogeneous composition of Gibberellin A-3 in a lipophilic solvent was developed.

A solvent system was first prepared as follows.

| Solvent system A | |
|---|---|
| Component | Weight (g) |
| Ecoteric T-80 | 63 |
| Esterol 123 | 702 |
| Esterol 244 | 135 |
| Water | 5 |

This mixture was stirred until it cleared.

A series of compositions were prepared with 10%, 3% and 1% concentrations of Gibberellin A-3. The Gibberellin A-3 powder was dispersed in the solvent system and then the other components added. The mixture was then stirred for 1–2 hours until clear.

Sample with 10% Gibberellin A-3

| Component | Weight (g) |
|---|---|
| Ethanol | 6.0 |
| Gibberellic acid | 23.5 |
| NORAM-O | 21.0 |
| Solvent system A | 157.5 |
| Water | 3.0 |

The mixture was stirred at 40° C. and ethanol added to produce a less viscous product. Other non-flammable viscosity reducing co-solvents are used in later examples.

Sample with 3% Gibberellin A-3

| Component | Weight (g) |
|---|---|
| Gibberellic acid | 16.0 |
| NORAM-O | 16.0 |
| Solvent system A | 454.0 |

Sample with 1% Gibberellin A-3

| Component | Weight (g) |
|---|---|
| Gibberellic acid | 2.25 |
| NORAM-O | 2.75 |
| Solvent system A | 195.00 |

Example 2

In this example, the effect of a lipophilic solvent-based solvent system on the efficacy of Gibberellin A-3 was investigated.

Composition Tested

| Components | w/w |
|---|---|
| Ecoteric T-80 | 29.0 |
| Esterol 123 | 324.0 |
| Esterol 244 | 62.3 |
| Gibberellic acid | 54.0 |
| NORAM-O | 41.5 |
| Water | 6.2 |

This formulation was prepared by mixing the components in the above order with stirring and warmed to 40° C. until clear.

Method

A field of grape vines at Irymple, Victoria, was divided into four separate plots. The sprays for sizing were applied at night, the first when 50% of the bunches had reached 4–6 mm berry size with a repeat application three days later and a final application five days after the second. The treatments were applied at a spray rate of 1500 liters of water per acre. Each plot was treated with a different composition as described below. The Control was the usual Gibberellin A-3 (ProGibb 10) in methanol solution. The other three plots tested the Experimental composition at three different application rates.

| Rate | ml (per 100 litres of water) |
|---|---|
| Control | 33.0 |
| Experiment 1 | 23.4 (approximately 75% normal Gibberellin A-3 rate) |
| Experiment 2 | 15.6 (approximately 50% normal Gibberellin A-3 rate) |
| Experiment 3 | 7.8 (approximately 25% normal Gibberellin A-3 rate) |

The grapes were harvested about two and half months later. The evaluation was undertaken by an independent assessor from the Melbourne Fruit Market 3 days after harvest.

Results

At the time of the harvest, the grapes from each plot were commercially acceptable and had no significant variation in colour. That is, even though less Gibberellin A-3 was used in Experiments 1, 2 and 3, equivalent results were obtained to the Control. Although of overall similar size, the grapes from Experiment 2 contained the greatest proportion of larger sized berries.

Conclusion

From the above results, it is evident that the efficacy of the Gibberellin A-3 is superior when carried in the new lipophilic solvent-based system than in methanol. Indeed, equivalent if not better results are evidenced from half as much Gibberellin A-3 as was previously used.

Example 3

Compositions tested

| | |
|---|---|
| Control | untreated |
| Treatment 1 | ProGibb 4% |
| Treatment 2* | 4% Gibberellin A-3 in lipophilic solvent-based solvent system |
| Treatment 3* | 2% Gibberellin A-3 in lipophilic solvent-based solvent system |

*Treatments 2 and 3 had the following compositions (w/w):

| Component | Treatment 2 | Treatment 3 |
|---|---|---|
| Ecoteric T-80 | 6.3 | 6.6 |
| Esterol 123 | 70.9 | 74.2 |
| Esterol 244 | 13.7 | 14.2 |
| Gibberellic acid | 4.4 | 2.2 |
| NORAM-O | 4.0 | 2.0 |
| Water | 0.7 | 0.8 |

Method

The treatments were tested both for thinning and sizing purposes at a farm in California, USA. All thinning treatments were applied to provide 8 g Gibberellin A-3 per acre (i.e. 200 g of Treatments 1 and 2, and 400 g of Treatment 3 were used). The spray rate was 200 US-gallons per acre at the time when the bloom was approximately 80%. All sizing treatments used 32 g Gibberellin A-3 per acre, with 3 days between applications.

Results

During the trials the spreading characteristics of the invention's solvent system were superior to that of the methanol system. At harvest time, the number of scarred berries per cluster had been reduced for the grapes treated with Treatments 2 and 3.

The thinning treatments were evaluated following berry set (approximately 2 weeks after bloom). Berry set is a measurement of the achievement of thinning. This is determined by measuring the length and number of berries of the upper shoulder of bunches (berry number per cm shoulder length) and the berry set calculated as the berry number per cm shoulder length.

| Treatment | Berry set |
| --- | --- |
| Control | 4.64 |
| Treatment 1 | 3.94 |
| Treatment 2 | 3.95 |
| Treatment 3 | 3.41 |

With lower numbers to be preferred, Treatment 3 provided the best results; Treatments 1 and 2 were similar whilst all three Treatments were superior to the Control.

The grapes were harvested at maturity to compare berry weight, length and displacement.

| Treatment | Weight (g) | Length (in) | Displacement (ml) |
| --- | --- | --- | --- |
| Control | 1.69 | 0.602 | 1.52 |
| Treatment 1 | 3.54 | 0.853 | 3.23 |
| Treatment 2 | 3.59 | 0.857 | 3.25 |
| Treatment 3 | 3.58 | 0.871 | 3.27 |

Each of the Treatments 1, 2 and 3 gave significantly larger berries than the Control as shown by average weight, length and displacement. Treatment 2 and 3 gave slightly larger berries than Treatment 1. Treatment 3 gave berries which were longer and of larger volume than Treatment 2. With all the Treatments having the same level of Gibberellin A-3, the improvements in berry quality can be related to the replacement of the methanol with the lipophilic solvent.

Example 4

Further laboratory work was undertaken to obtain homogeneous compositions, the following being examples of such:

| Composition | A | B | C | D |
| --- | --- | --- | --- | --- |
| AT 1214 | 6 | 5 | 6 | 7.5 |
| Butyl Diglysolv | 2.8 | 8.5 | 11 | 11 |
| Butyl Glysolv | 0.9 | | | |
| Ecoteric T-80 | 4 | 5 | 4 | 4 |
| Esterol 123 | 55 | 55 | 55 | 55 |
| Esterol 244 | 9.2 | 10.5 | 9 | 9 |
| Ethanol | 0.3 | | | |
| Ethyl Diglysolv | 6.4 | | | |
| Gibberellic acid | 11 | 11 | 11 | 11 |
| Glysolv DPM | 0.6 | | | |
| NORAM-O | 4 | 5 | 4 | 2.5 |

Composition D was subjected to stability testing. The standard accelerated test showed no loss of active after 56 days at 40° C. or 56 days at 2° C.

Example 5

In this example a field trial was conducted with Gibberellin A-3 carried in a lipophilic solvent system.

Compositions Tested Were

| | |
| --- | --- |
| Treatment 1 | ProGibb 10 |
| Treatment 2 | 10% Gibberellin A-3 in lipophilic solvent system. Composition A from Example 4 was used as the lipophilic solvent system for the Thinning and Composition D from Example 4 was used as the lipophilic solvent system for the Sizing sprays. |

Method

The trials were undertaken at a farm at Redcliffs, Victoria. The produce was mostly table grapes for the export market. Within the field of grape vines, 6 strands were allocated to the experimental product. Both Treatments 1 and 2 were applied using a 1500 liter tank per acre of crop as follows:

| Application Timing | Spray type | Treatment 1 or 2 Solution. (ml in tank) | X-77 (ml in tank) | Urea Phosphate* (ml in tank) |
| --- | --- | --- | --- | --- |
| 40–50% bloom | Thinning 1 | 200 | 150 | — |
| 3 days later | Thinning 2 | 200 | 150 | — |
| 4–6 mm berry size | Sizing 1 | 500 | 150 | 2000 |
| 5 days later | Sizing 2 | 500 | 150 | 2000 |
| 11 days later | Sizing 3 | 700 | 150 | 2000 |

*Urea phosphate is a common fertilizer used in the district and applied with sizing treatments.

Results

At the time of spraying Sizing 1, the grapes from the new product were visually slightly larger. This observation was again repeated at the time of spraying Sizing 2.

The grapes from both treatments were harvested on the same day and assessed. The overall impression was that the experimental grapes had run 2–3 days ahead to maturity. This is of significant value for any farmer with inclement and thus destructive weather being expected at any time.

Three or four random bunches (approx. 2 kg) were picked from each plot and were assessed for berry size and density. The impact and hence value to the consumer comes from the overall size of the larger grapes which visually dominate and thus affect the value. With at least 8 berries from each bunch, a total of 40 berries (visual selection) were picked from each trial

| Treatment | Average Weight (g/berry) | Average density (ml/g) |
| --- | --- | --- |
| 1 | 5.03 | 0.93 |
| 2 | 5.80 | 0.94 |

A smaller number of the next larger berries were then assessed

| Treatment | Average Weight (g/berry) | Average density (ml/g) |
|---|---|---|
| 1 | 4.99 | 0.926 |
| 2 | 5.21 | 0.935 |

Conclusion

Table grapes of superior quality, and thus sale value, were apparent by increasing the size of grapes achieving grape maturity at an earlier date obtaining more visually attractive berries eliminating the undesirable flammable/poisonous carrier Preferably, the composition is applied to the fruit (eg. grapes) in multiple steps with time breaks between applications dependent on crop maturity. The application rate of the gibberellins in the spray solution can be around 10 ppm for thinning and 30 ppm for sizing. Typically, the active ingredient is incorporated in amounts in the range of 4 to 10% weight to volume in the composition. Amounts in the range of 1 to 75 ml of such compositions are typically added to 100 L of water for application (1 to 30 ppm gibberellins). Further, typical application rates of such formulations are in the range of 1000 L to 2000 L of water per acre.

Example 6

The following composition was prepared.

| Component | w/w |
|---|---|
| AT 1214 | 92.4 |
| Butyl Diglysolv | 132 |
| Ecoteric T-80 | 39.6 |
| Esterol 123 | 620.4 |
| Esterol 244 | 105.6 |
| GA4/7 | 132 |
| NORAM-O | 26.4 |

This is a stable clear liquid formulation.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A plant growth promoter composition comprising:
   (a) not in excess of 20% by weight of the total composition of one or more gibberellins; and
   (b) an essentially non-aqueous solvent system comprising:
      (i) 30 to 99% by weight of the total composition of one or more lipophilic solvents;
      (ii) one or more lipophilic alkaline coupling agents which enable the gibberellins to form a lipophilic solvent soluble complex, wherein the amount of lipophilic alkaline coupling agents is more than the equivalent molar amount of gibberellins;
      (iii) 1 to 50% by weight of the total composition of one or more emulsifiers which blend with the lipophilic solvent(s) to form a homogeneous product and enable dispersion of the composition into water for application; and
      (iv) optionally, not in excess of 15% by weight of the total composition of one or more viscosity reducing co-solvents.

2. The plant growth promoter composition according to claim 1 wherein the gibberellin is gibberellic acid (Gibberellin A-3).

3. The plant growth promoter composition according to claim 1 wherein the amount of gibberellin(s) is in the range of 1 to 15% by weight of the total composition.

4. The plant growth promoter composition according to claim 3 wherein the amount of gibberellin(s) is in the range of 4 to 10% by weight of the total composition.

5. The plant growth promoter composition according to claim 1 wherein the lipophilic solvent is one or more esters of vegetable oils.

6. The plant growth promoter composition according to claim 5 wherein the esters of vegetable oils are one or more alkyl esters of fatty acids.

7. The plant growth promoter composition according to claim 1 wherein the amount of lipophilic solvent is in the range of from 40 to 80% by weight of the total composition.

8. The plant growth promoter composition according to claim 1 where in the lipophilic alkaline coupling agent is selected from the group consisting of quarternary ammonium hydroxides, overbased phenates, overbased sulphonates, aromatic amines, arylalkyl amines, alkylaryl amines, polycyclic amines, fatty amines, fatty imidazolines and mixtures thereof.

9. The plant growth promoter composition according to claim 8 wherein the lipophilic alkaline coupling agent is a mixture of dimethylcocoamine and oleylamine.

10. The plant growth promoter composition according to claim 1 wherein the amount of lipophilic alkaline coupling agent is in molar excess to the amount of gibberellin(s).

11. The plant growth promoter composition according to claim 10 wherein the amount of lipophilic alkaline coupling agent is about 30% more than the equivalent molar amount of gibberellin(s).

12. The plant growth promoter composition according to claim 1 wherein the amount of emulsifier is in the range from 3 to 20% by weight of the total composition.

13. The plant growth promoter composition according to claim 1 wherein the viscosity reducing co-solvent is selected from the group consisting of glycol, diglycol, diglycol ether and mixtures thereof.

14. A method for enhancing the efficacy of at least one gibberellin as a plant growth promoter comprising the step of incorporating gibberellins into an essentially non-aqueous solvent system to form a plant growth promoter composition, the solvent system comprising:
   (i) 30 to 99% by weight of one or more lipophilic solvents;
   (ii) at least an equivalent molar amount to the gibberellins of one or more lipophilic alkaline coupling agents which enable the gibberellin(s) to form a lipophilic solvent soluble complex;
   (iii) 1 to 50% by weight of one or more emulsifiers which blend with the lipophilic solvent(s) to furnish a homogeneous product and enable dispersion of the composition into water for application; and
   (iv) optionally, not in excess of 15% by weight of one or more viscosity reducing co-solvents; wherein the resultant plant growth promoter composition may be directly applied to a plant.

15. The method according to claim 14 wherein the gibberellin is gibberellic acid (Gibberellin A-3).

16. The method according to claim 14 wherein the amount of gibberellin(s) is in the range of 1 to 15% by weight of the total composition.

17. The method according to claim 16 wherein the amount of gibberellin(s) is in the range of 4 to 10% by weight of the total composition.

18. The method according to claim 14 wherein the lipophilic solvent is one or more esters of vegetable oils.

19. The method according to claim 18 wherein the esters of vegetable oils are one or more alkyl esters of fatty acids.

20. The method according to claim 14 wherein the amount of lipophilic solvent is in the range of from 40 to 80% by weight of the total composition.

21. The method according to claim 14 where in the lipophilic alkaline coupling agent is selected from the group consisting of quarternary ammonium hydroxides, overbased phenates, overbased sulphonates, aromatic amines, arylalkyl amines, alkylaryl amines, polycyclic amines, fatty amines, fatty imidazolines and mixtures thereof.

22. The method according to claim 21 wherein the lipophilic alkaline coupling agent is a mixture of dimethylcocoamine and oleylamine.

23. The method according to claim 14 wherein the amount of lipophilic alkaline coupling agent is more than the equivalent molar amount of gibberellins.

24. The method according to claim 23 wherein the amount of lipophilic alkaline coupling agent is 30% more than the equivalent molar excess of gibberellins.

25. The method according to claim 14 wherein the amount of emulsifier is in the range from 3 to 20% by weight of the total composition.

26. The method according to claim 14 wherein the viscosity reducing co-solvent is selected from the group consisting of glycol, diglycol, diglycol ether and mixtures thereof.

* * * * *